US008795956B2

(12) United States Patent
Esperester et al.

(10) Patent No.: US 8,795,956 B2
(45) Date of Patent: Aug. 5, 2014

(54) METHOD FOR THE ANTI-INFLAMMATORY PROTECTION OF TRANSPLANTS USING QUERCETIN GLUCURONIDE

(75) Inventors: Anke Esperester, Mainz (DE); Stephan Nees, Munich (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 361 days.

(21) Appl. No.: 12/919,563

(22) PCT Filed: Mar. 3, 2009

(86) PCT No.: PCT/EP2009/052503
§ 371 (c)(1),
(2), (4) Date: Nov. 12, 2010

(87) PCT Pub. No.: WO2009/109574
PCT Pub. Date: Sep. 11, 2009

(65) Prior Publication Data
US 2011/0129809 A1 Jun. 2, 2011

(51) Int. Cl.
*A01N 1/00* (2006.01)
(52) U.S. Cl.
USPC .......................................................... 435/1.1
(58) Field of Classification Search
CPC .................................................... A01N 1/0226
See application file for complete search history.

(56) References Cited

U.S. PATENT DOCUMENTS

| 6,485,727 | B1 | 11/2002 | Esperester et al. |
| 6,991,816 | B2 | 1/2006 | Esperester et al. |
| 7,270,838 | B2 | 9/2007 | Esperester et al. |
| 7,674,488 | B2 | 3/2010 | Masuda et al. |
| 2003/0031739 | A1 | 2/2003 | Esperester et al. |
| 2004/0062824 | A1 | 4/2004 | Esperester et al. |
| 2004/0151769 | A1 | 8/2004 | Esperester et al. |
| 2004/0151794 | A1 | 8/2004 | Sacher et al. |
| 2005/0053560 | A1 | 3/2005 | Petrini et al. |
| 2005/0142235 | A1 | 6/2005 | Horie et al. |
| 2005/0142236 | A1 | 6/2005 | Horie et al. |
| 2005/0151794 | A1 | 7/2005 | Silverbrook et al. |
| 2005/0202110 | A1 | 9/2005 | Horie et al. |
| 2005/0271757 | A1 | 12/2005 | Masuda et al. |
| 2006/0068043 | A1 | 3/2006 | Esperester et al. |
| 2006/0198913 | A1 | 9/2006 | Sacher et al. |
| 2007/0198913 | A1 | 8/2007 | Terao et al. |
| 2011/0053874 | A1 | 3/2011 | Esperester et al. |
| 2011/0129809 | A1 | 6/2011 | Esperester et al. |
| 2011/0200539 | A1 | 8/2011 | Buszello et al. |

FOREIGN PATENT DOCUMENTS

| EP | 1057405 | A1 | 12/2000 |
| EP | 1435242 | A1 | 7/2004 |
| EP | 1535514 | A1 | 6/2005 |
| WO | 03099307 | A1 | 12/2003 |
| WO | 2004058280 | A1 | 7/2004 |

OTHER PUBLICATIONS

Nugent et al., "Endothelial Implants Inhibit Intimal Hyperplasia After Porcine Angioplasy", Circulation Research 84 : 384-391 (1999).*
Vrhovsek et al., "A Versatile Targeted Metabolomics Method for the Rapid Quantfication of Multiple Classes of Phenolics in Fruits and Beverages", J. Agricultural and Food Chemistry 60 : 8831-8840 (2012) and 20 pages of supporting information.*
Vrhovsek et al., Supporting Information for above publication J. Agricultural and Food Chemistry 60 (2012), 20 pages.*
Castillo-Munoz, N. et al. "Flavonol profiles of Vitis vinifera red grapes and their signle-cultivar wines". Journal of Agricultural and Food Chemistry. Bd 55, No. 3, Feb. 2007, p. 992.
Chem Abstract—139:173507, 2003, Schaefer."Edema protective properties of the red vine leaf extract AS 195 (Folia vitis viniferae) in the treatment of chronic venous insufficiency" A 6-week observational clinical trial.
Chem Abstract—PREV200500205124, Mochizuki, 2004. "Effect of quercetin conjugates on vascular permeability and expression of adhesion molecules".
Esperester, A. et al. "Quercetin-glucuronide (QG) prevents microcirculatory complications acutely caused by simultaneously activated PMN and platelets (P) in the human heart". Circulation, Bd.110, No. 17, Suppl. S, Oct. 2004, p. 126.
Fantinelli, J. et al. "Cardioprotective effects of a non-alcholic extract of red wine during ischaemia and reperfusion in spontaneously hypertensive rats". Clinical and Experimental Pharmacology and Physiology. Bd. 34, No. 3, Mar. 2007, p. 166.
International Search Report for PCT/EP2009/052503 mailed Jul. 16, 2010.
Kiesiwetter, H. "Efficacy of Orally Administered Extract of Red Vine Leaf as 195 (Folia Vitis Viniferae) in Chronic Venous Insufficiency (Stages I-III) A Randomized, Double-Blind Placebo-Controlled Trial". Drug Research, Bd. 50, No. 2, Jan. 1, 2000, p. 109.
Lodi, F. et al. "Protective effects of quercetin and its metabolites on endothelial dysfunction in rat aorta". FASEB Journal, Fec. of American Society for Experimental Biology—Meeting Abstracts, US, Bd 21, No. 6, 1, 2007, p. A1172.
Nees, S. et al. "Protective effects of flavonoids contained in the red vine leaf on venular endothelium against the attack of activated blood components in vitro". Arzeneimittal Forschung. Drug Research, ECV Ediotio Cantor Verlag, Aulendorf, DE, Bd 53, No. 5, 2003, p. 330-341.
Tribolo, S. et al. "Comparative effectsof quercetin and its predominant human metabolites on adhesion molecule expression in activiated human fascular endothelial cells". Atherosclerosis, Elsevier Ireland Ltd, 2008, Bd 197, No. 1, p. 50-56.
U.S. Appl. No. 12/919,561, filed Aug. 26, 2010. Inventor: Anke Esperester. Title of Invention: Use of flavonoide compounds for the prophylasis and therapy of ischaemic or inflammatory heart and cardiovascular diseases.
U.S. Appl. No. 12/674,914, filed Feb. 24, 2010, Inventor: Katrin Buszello, Title of Invention: Sprayable composition comprising extract of red vine leaves.

* cited by examiner

*Primary Examiner* — Sandra Saucier
(74) *Attorney, Agent, or Firm* — Michael P. Morris; David L. Kershner; Usha R. Patel

(57) ABSTRACT

The invention relates to a method for protecting transplants, as well as organs and individual blood vessels, against inflammatory reactions that are caused by the operative procedure linked to the explantation and storage until transplantation. This can be achieved by treating the transplant via intra arterial application of flavonol compounds, in particular with quercetin glucuronide and/or kaempferol glucuronide.

4 Claims, No Drawings

METHOD FOR THE ANTI-INFLAMMATORY PROTECTION OF TRANSPLANTS USING QUERCETIN GLUCURONIDE

SCOPE OF THE INVENTION

The present invention relates to additives to organ preservation solutions for protecting biological transplants of all kinds (tissues, blood vessels, organs), after they have been explanted and during their storage or transportation, from ischaemically induced inflammatory reactions (e.g. oedema and/or cell damage caused by oxidation or hydrolysis), which are triggered by the temporary cessation of blood flow. This is achieved by the addition of certain flavonoids of the flavonol group, particularly quercetin glucuronide and/or kaempferol glucuronide, to the preservation solutions in question.

BACKGROUND TO THE INVENTION

It is known that after ischaemia and reperfusion of organs or individual blood vessels with blood, the inflammation mediators that are unavoidably released from damaged tissue or from tissue that is healthy in principle but ischaemically damaged cause platelets and neutrophilic granulocytes (PMN) to be activated. If these two types of blood cell are activated at the same time, platelet-activating factor (PAF) and leukotriene $B_4$ ($LTB_4$) are synthesised and released, which may selectively and synergistically activate the endothelium of the respective organ venules and also the macrovenous luminal endothelium to contract and open its intercellular spaces. As a result, the outflow of plasma components (e.g. clotting factors, complement factors and platelets) into the respective interstitial space of the organs in question is greatly increased. At the same time, PAF and $LTB_4$ promote the stickiness of the platelets and PMN at the respective endothelium. As sticky leukocytes can damage the endothelium by releasing aggressive compounds (e.g. proteolytic enzymes, oxygen radicals, hypochlorous acid, etc.) and activated platelets on the surface become catalysts of a fibrin formation extending around them by binding and arranging the clotting cascade, inflammatory reactions occur on the wall and in the lumen of affected blood vessels, leading to the formation of clots. These inflammatory processes may spread within organs to smaller blood vessels located downstream. A consequence of inflammations of this kind spreading to the microcirculation is that there is a massive accumulation of white corpuscles inside and around the smallest veins (post-capillary venules) which may induce extensive inflammatory oedema in organs. In addition, there is a high probability that arterioles located in the vicinity will constrict, through the opening of the venular barrier and numerous inflammation mediators, and as a result local bloodflow will be severely restricted. There is also the risk of intravascular thromboses.

If for example organs in a human being suffer from a deficient blood supply during an operation or after explantation, as a rule the inflammatory processes described hereinbefore will generally occur within the respective microvascular systems. In bypass operations in which organ arteries occluded thrombotically or by thickening of the vascular wall are bridged by healthy vascular segments sutured in (often taken from non-essential peripheral veins, less frequently from arteries), there is often the additional problem that the endothelium of the transplanted vascular segments is itself damaged. The high acute restenosing rates of grafts after coronary bypass operations, which have been particularly well studied in this respect (30-40% restenosis even within the first post-operative year!) speak for themselves, and many others become occluded in the decade that follows.

The aim is therefore to protect transplants from the occurrence of the inflammations described above.

SUMMARY OF THE INVENTION

It has now been found that the inflammations described hereinbefore virtually do not occur at all in the presence of certain flavonoids of the flavonol group, particularly quercetin glucuronide and kaempferol glucuronide, or can be made reversible. With the aid of this finding, the effect of flavonol compounds (quercetin glucuronide and/or kaempferol glucuronide) as an addition to current organ preserving solutions has been tested.

DETAILED DESCRIPTION OF THE INVENTION

"Transplants" in the sense of the present invention are tissues, individual blood vessels, organs or parts of the human body which have been removed from a donor body for implanting in a recipient body. The recipient body may be the donor body or a different body.

Inflammatory processes in the sense of the present invention are defence processes induced acutely or chronically by components of the immune system, in which not only foreign substances, foreign cells, foreign tissue or transplanted body parts that have entered a body, but also the body's own structures, cells, tissues and body parts may fail. These processes that cause direct cell damage are instigated by the activity of hydrolytic defence enzymes, oxidants and phagocytes of the immune system. Cell-aggregatory, thrombotic and oedematous processes develop in parallel and may have a pathogenic effect on the affected body regions in the course of ischaemic disorders. Under healthy, "normal" conditions, no extensive inflammatory disorders occur in organs. The inflammatory conflict between the body and its environment that is unavoidable in normal life, e.g. within the scope of "everyday" wound infections, leads to a physiological immune response which restricts foreign structures and/or pathogens to local areas of infection or lesion. Inflammatory processes of this kind (which may almost be termed "physiological") are soon eliminated again by the regeneration and healing processes induced by the inflammation.

"Blood vessels" in the sense of the present invention are all the regions through which blood flows in the human body. These include in particular the heart, veins and venules and arteries and arterioles.

"Flavonol compounds" in the sense of the present invention are substances with a 3-hydroxyflavone structure, particularly those with free hydroxyl groups. Preferred flavonols are derivatives of quercetin and kaempferol. Particularly preferred flavonol compounds within the scope of the present invention are quercetin glucuronide and kaempferol glucuronide, particularly quercetin-3-O-β-D-glucuronide and kaempferol-3-O-β-D-glucuronide.

"Venules" in the sense of the present invention are tiny veins located postcapillary in the circulatory system, with a cross-section of 10-30 μm.

"Arterioles" in the sense of the present invention are tiny arteries with a cross-section of 10-50 μm The "inner surface" of a transplant in the sense of the present invention relates to the luminal surface of the blood vessels of the transplant which, after removal from the donor body, are perfused with suitable preserving solution from outside.

The "outer surface" of a transplant in the sense of the present invention relates to the surface of the transplant which is visible to the outside observer with the naked eye.

The transplantation process can be divided into three phases:

In the first phase the transplant is surgically removed from the donor organism. In this first phase, first irritations are triggered which may then further promote physiological cascades leading to inflammation.

In the second phase the transplant is stored in a suitable preservation solution in an ischaemic state, i.e. there is no longer blood flowing through it, as it is outside a body providing a blood supply. This second or ischaemic phase is extremely critical for the subsequent behaviour of the transplant. If the inflammation cascade induced in the first phase is allowed to proceed, there may be serious complications during the ischaemic storage of the transplant which will call into question the success of the entire transplantation process. On the other hand, in the ischaemic phase there is a particularly simple opportunity to act deliberately on the transplant in order to mitigate or even suppress precisely the cascade reactions described that lead to inflammation. This is the crux of the present invention.

In the third phase, the transplant is implanted in the recipient organism. This phase is also known as the reperfusion phase, as blood flows through the transplant once more. According to earlier understanding, paradoxically, the worst damage is often done to the transplant at the very moment when the organ that has become ischaemic is finally perfused with blood once again. Nowadays we know that this is precisely when fresh granulocytes and platelets may begin their pathogenic cooperation, which then leads to the opening of the venular endothelial bather and the subsequent inflammatory processes.

Various flavonoid compounds have already often been found to be highly effective anti-inflammatories. It has been found, inter alia, that quercetin glucuronide can strongly inhibit the synthesis of PAF and LTB4 carried out by activated platelets and thereby prevent pathological opening up of the venular endothelial barrier. At the same time, analogously to the manner described hereinbefore, this sharply reduces the activation and stickiness of the blood cells on the endothelial surface.

A number of flavonoid compounds have been demonstrated to have an anti-inflammatory activity on cell lines and in animal trials. However, the relevance of the results to the protection of human organs was unclear.

The present invention makes use of the findings described above in order to suppress the inflammatory processes and their triggers in the ischaemic phase or preoperative storage phase, by treating the transplants taken from the donor body with flavonol compounds, particularly quercetin glucuronide and kaempferol glucuronide, and thus prevent the complications described above, such as occlusion of freshly implanted bypasses and the like after implantation and reperfusion of the transplants in the recipient body.

Optimised Procedure for Preserving Organs that are Intended for Transportation and Subsequent Transplantation The explanted organs (hearts, lungs, kidneys, etc.) are ideally flushed through in situ at room temperature, before the explantation, with heparin-anticoagulated preservation solutions to which quercetin glucuronide has previously been added to give a final concentration of 100 µM. After the blood has been washed out as completely as possible, the organs are placed in fresh, analogously substituted preservation solution and cooled to 4° C. In this state, the organs can be stored for up to 12 h and then transplanted.

The recommended basic solutions are the following 2 solutions which in our experience are both roughly equally suitable (concentrations, unless stated otherwise, are given in brackets in mM):

1. UW solution ("University of Wisconsin solution").
    K lactobionate (100), $NaKH_2PO_4$ (25), $MgSO_4$ (5), glutathione (3), raffinose (30), allopurinol (1), adenosine (5), penicillin (200 U), insulin (40 U), dexamethasone (16 mg), hydroxyethyl starch (5 g %), Na (30), K (120). The pH is adjusted to 7.4, the osmolarity is found to be 320-330 mOsmol/l.
2. Histidine-tryptophan-ketoglutarate solution ("Bretschneider solution")
    NaCl (15), KCl (9), $MgCl_2$ (4), mannitol (30), histidine (180), histine/HCl (18), tryptophan (2), K-ketoglutarate (1). The pH is adjusted to 7.1, the osmolarity is found to be 300 mOsmol/l.

Before use, 100× concentrated aqueous stock solution of quercetin glucuronide adjusted to pH 7.4 is added to these solutions to give a final concentration of 100 µM. When frozen, this stock solution of the flavonoid can be stored for at least 6 months at −80° C.

Preservation Procedure for Guinea Pig Hearts

Female guinea pigs (250-330 g) were used as heart donors. After the animals were decapitated their hearts were explanted and placed in a Langendorff apparatus (specially constructed). Perfusion was carried out retrogressively through the aorta under normal conditions under a constant pressure of 60 mmHg for 3 min (mode 1). Krebs-Henseleit-bicarbonate buffer (KHM) which was gassed with carbogen before use was used for the perfusion, without added quercetin glucuronide (QG), at a temperature of 37° C. After cannulation of the left atrium, the apparatus was switched to operating mode (mode 2) with a preload of 10 mmHg and an afterload of 60 mmHg After 2 minutes' perfusion the basic functions were recorded, specifically: aortic flow, coronary flow, ejection rate, heart rate, maximum systolic pressure, mean arterial pressure, and the product of the heart rate and maximum systolic pressure. Then the apparatus was switched to mode 1, and the hearts, divided into 2 groups, were perfused further with HTK solution chilled to a temperature of 4° C. (=Bretschneider's cardioprotective solution), with or without the addition of 100 µM QG, until the heart stopped in each case, and then stored in the dark at 4° C. in the same perfusion medium (30 ml in each case) for a period of 8 h. Then the hearts were placed in the Langendorff apparatus once again and perfused under normal conditions in mode 1. Finally, the apparatus was switched back into operating mode and the performance data defined above were measured under these conditions as well. Result: All the values measured in the hearts preserved with the addition of QG during the 8 hour ischaemic period were 25-35% above those of the comparison hearts (no QG added to the HTK solution).

The invention claimed is:

1. Process for protecting transplants from the formation of inflammation in blood vessels, comprising:
    a) removing the transplant,
    b) treating the said transplant with 100 uM of quercetin glucuronide, and
    c) re-implanting the said treated transplant into a recipient body;
    wherein, the transplant is an organ, blood vessels or a combination of both, and wherein each organ, blood vessel or a combination of both has an inner surface and an outer surface.

2. The process according to claim 1, wherein the quercetin glucuronide is used as an ingredient of a solution or suspension.

3. The process according to claim 2, further comprising flushing the said blood vessels of the transplant with the said solution or suspension so that the inner surface of the transplant is in contact with the solution or the suspension.

4. The process according to claim 2, further comprising placing the transplant in the said solution or suspension wherein the inner and outer surfaces of the transplant are in contact with the solution or suspension.

* * * * *